United States Patent [19]

Lloyd-Jones et al.

[11] Patent Number: 5,051,253

[45] Date of Patent: Sep. 24, 1991

[54] USE OF POLYACRYLATES TO REDUCE PROTEOLYTIC ACTIVITY IN THE HUMAN INTESTINAL TRACT

[75] Inventors: John G. Lloyd-Jones, Cottingham; Peter W. Dettmar, Welwick, both of United Kingdom

[73] Assignee: Reckitt & Colman Products Limited, United Kingdom

[21] Appl. No.: 377,115

[22] Filed: Jul. 7, 1989

[30] Foreign Application Priority Data

Jul. 16, 1988 [GB] United Kingdom ................. 8817015

[51] Int. Cl.$^5$ ............................................. A61K 31/78
[52] U.S. Cl. ..................................................... 424/81
[58] Field of Search ............................................ 424/81

[56] References Cited

U.S. PATENT DOCUMENTS

| | | | |
|---|---|---|---|
| 2,909,462 | 10/1959 | Warfield et al. | 167/56 |
| 3,930,005 | 12/1975 | Wojnor et al. | 514/261 |
| 4,273,761 | 6/1981 | Matsuda et al. | |
| 4,705,683 | 11/1987 | Dettmar | 424/81 |

FOREIGN PATENT DOCUMENTS

| | | | |
|---|---|---|---|
| 2815891 | 10/1978 | Fed. Rep. of Germany | 424/81 |
| 59-196825 | 4/1983 | Japan | 424/81 |
| 59-163310 | 7/1983 | Japan | 424/81 |
| 1005687 | 9/1965 | United Kingdom . | |
| 1435630 | 5/1976 | United Kingdom . | |
| 1538123 | 1/1979 | United Kingdom . | |
| 1538352 | 1/1979 | United Kingdom . | |

OTHER PUBLICATIONS

Marshall, "The Isolation and Characterization of the High-Molecular-Weight Glycoprotein from Pig Colonic Mucus", Biochem J. (1978), 173, 569-578.

Ishii, "Effects of Sodium Polyacrylate (PANa) on Peptic Ulcers in Rats", Oyo Yakuri (1982) 23 (1) 55-62.

Hill, "The Possible Role of Bacteria in Inflammatory Bowel Disease", Current Concepts in Gastroenterology, Winter 1985, pp. 8-13.

*Primary Examiner*—Merrell C. Cashion, Jr.
*Assistant Examiner*—Peter F. Kulkosky
*Attorney, Agent, or Firm*—Bacon & Thomas

[57] ABSTRACT

A method for the treatment of inflammatory bowel disease which comprises administering to a patient an effective oral or rectal amount of a polyacrylate. There are also described compositions for use in the method.

6 Claims, No Drawings

USE OF POLYACRYLATES TO REDUCE PROTEOLYTIC ACTIVITY IN THE HUMAN INTESTINAL TRACT

This invention relates to the use of polyacrylates and in particular to carbomer, in the treatment of inflammatory bowel disease.

The polyacrylates are high molecular weight resins which may be linear or cross-linked. They find wide application as suspending agents in industries such as the oil, cosmetic and pharmaceutical industries.

Sodium polyacrylate has been suggested for use in the treatment of peptic ulcers. British patent No. 1435630 (Nippon Kayaku) describes a solid antipeptic ulcer composition comprising sodium polyacrylate having an intrinsic viscosity of 0.3 or more and a pharmaceutically inert solid carrier. British patent No. 1538352 (Nippon Kayaku) describes an improved composition which comprises granules of polyacrylic alkali metal salt coated with a water-insoluble but water permeable coating agent such as ethyl cellulose. Suitable polyacrylic alkali metal salts are stated to include sodium polyacrylate of molecular weight 3,000,000 to 8,000,000. The only specific sodium polyacrylate mentioned is one of molecular weight about 3,400,000.

Further investigations at Nippon Kayaku on coated granules of a sodium polyacrylate are described in Effects of Sodium Polyacrylate (PANa) on Peptic Ulcers in Rats (Ishii and Fujii, Oyo Yakuri, 23 (1), 55–62, 1982). It was concluded that the coated PANa had not only a preventive effect against ulceration in the fore-stomach, stomach and duodenum but also an accelerating effect on healing of gastric ulcers in rats. PANa had weak antipepsin activity and had practically no inhibiting action against trypsin or chyrotrypsin i.e. PANa had only limited anti-protease action.

Carbomer is described in the British Pharmacopeia and the U.S. National Formulary as being a synthetic high molecular weight cross-linked polymer of acrylic acid containing 56 to 68% of carboxylic acid groups. The British Pharmacopeia specifies cross-linking with allylsucrose. U.S. Pat. No. 2,909,462 describes the use as a bulk laxative of a colloidally water-soluble polymer of acrylic acid cross-linked with from about 0.75% to 2.0% of polyallyl sucrose.

In our U.S. Pat. No. 4,705,683 we describe synergistic combinations of histamine $H_2$-receptor antagonists, especially cimetidine, with sodium polyacrylates and especially with sodium carbomer for use in the treatment of gastritis or of gastro-duodenal ulcers.

Inflammatory bowel disease (IBD) is a collective term (encompassing ulcerative colitis and Crohn's disease) which describes a variety of clinical and pathological conditions of the gastrointestinal tract.

Ulcerative colitis is a diffuse, non-specific, inflammatory disease of poorly understood aetiology. It is essentially a mucosal lesion which involves the rectum and which may extend for a variable length of the colon. Crohn's disease is an acute or chronic granulomatous disease which may affect any part of the alimentary tract but is mainly found in the terminal ileum, large intestine or both and is characterised by multiple lesions with normal intestine intervening between them. The breakdown of the colonic mucosal barrier and changes in colonic mucus secretion are features of IBD. As mucus is the only barrier between the epithelial cells and the colonic lumen, it is considered an important part of the protective mechanisms in IBD and increased degradation of the mucus layer would compromise mucosal defence.

Mucus secreted viscoelastic gel adheres to and covers the gastrointestinal mucosal surface protecting it against mechanical shear, micro-organisms and the action of allergens and toxins. To form an effective gel the mucus glyco-protein must retain its native polymeric structure (Allen, Trends in Biochemical Sciences, 8 (5), 169–173, 1983). This is readily apparent following degradation of mucus gel, by proteolysis, to its glycoprotein subunits. These subunits have a lower intrinsic viscosity and provide a much weaker barrier.

There is substantial evidence suggesting a close association between the enteric microflora and IBD. The bacterial flora of the healthy gut is very stable and in symbiosis with the host. If this symbiotic relationship is disturbed, by for example altering the balance of the organisms, physical damage of the gut may result. Symptoms of inflammatory bowel disease are considered to be associated with bacterial overgrowth. (Hill, Current Concepts in Gastroenterology, 10 8–13 (4) 1985). Inflammatory bowel disease is considered to be a two stage process, with an initiation and a maintenance phase. It is unclear whether the initiation phase of the disease is associated with microflora changes, however there is substantial evidence of bacterial involvement in the maintenance phase of the disease.

It has been found from studies of proteolytic and glycosidase activity in stools of patients with ulcerative colitis and Crehn's disease (Corfield et al, Clinical Sciences 74 (1), 71–78, 1988) that there is a significant elevation in enzymic activity possibly of bacterial origin when compared to asymptomatic controls. Hence the pathogenesis of inflammatory bowel disease may well be related to the actions of such enzymes. It has been established (Hoskins, J. Clin. Invest. 67, 163–172, 1981) that enzymes of bacterial origin can readily degrade mucus glycoprotein thereby solubilising the surface gel and causing disruption of the colonic mucosal barrier.

The above observations have an important implication upon the understanding of the aetiology of colonic disease. Factors like elevated proteolytic activity contributing to increased mucus erosion result in a weakening or possible destruction of the surface mucus gel. Agents that can arrest this process through strengthening of the mucus barrier would protect against progression of the disease caused by pathogenic organisms.

We have previously shown that polyacrylates strengthen gastric mucus and protect against cellular damage by erosive agents through enhancement of native as well as degraded gel viscosity. Differences are known to exist in basic structure of the mucus glycoprotein of gastric and colonic origin (Marshall and Allen, Biochem. J. 173 569–578, 1978).

We have carried out investigations on the interaction of several polyacrylates and other acidic polymers with colonic mucus glycoprotein and have assessed their ability to inhibit mucolysis by faecal enzymes to see if any had the potential to alter the disease process by protecting the colonic mucosa.

We found that the polyacrylates, and particularly carbomer 934P, were superior to all other agents in their ability to produce a marked increase in viscosity of the mucus above the control value, this being the sum of the viscosity of mucus and polyacrylate alone. This was true for both degraded and undegraded mucus glycoprotein.

We also found that polyacrylates when compared to other acidic polymers totally inhibit the mucolytic protease activity found present in human faecal extracts. Other agents tested showed only a marginal effect.

According to the present invention there is provided the use of polyacrylates for the manufacture of a medicament for the treatment of inflammatory bowel disease.

By polyacrylate we mean polyacrylic acid and its pharmaceutically acceptable salts. Preferably the polyacrylate is carbomer or its sodium salt and most preferably carbomer 934P or its sodium salt.

The medicaments may be administered orally or rectally, as appropriate, according to the site of the disease.

In an aspect of the invention there is provided a method for the treatment of inflammatory bowel disease which comprises administering to a patient an effective oral or rectal amount of a polyacrylate.

U.S. Pat. No. 2,909,462-(mentioned above) discloses the use of polyacrylates in the treatment of lower gastro-intestinal disorders principally as laxatives. In the treatment of constipation therapeutic effectiveness of polyacrylates has been attributed to their ability to reduce water absorption by retaining water in the gut lumen. This action is entirely different to that described in the present invention and was not directed towards the treatment of ulcerative colitis or Crohn's disease.

The medicaments are for oral or rectal administration. As oral preparations they may be in the form of liquid compositions or solid compositions in the form of for example powders or granules, conveniently in unit dosage form in capsules or sachets. For rectal administration they may conveniently be in the form of aqueous retention enemas.

The following describes in more detail the types of presentation, methods for their preparation and examples thereof.

1. LIQUIDS

With aqueous liquid compositions which are susceptible to contamination and subsequent deterioration by micro-organisms, it is preferable to include a preservative. Suitable systems include combinations of methyl and propyl p-hydroxybenzoates (methyl parabens and propyl parabens).

Aqueous compositions containing neutralised carbomer at high concentration have a high viscosity which would render them unpourable. The viscosity is reduced by increasing the ionic strength of the solution using suitable salts. Suitable salts which are acceptable biologically include bicarbonate salts of sodium and potassium, or citrate salts.

The pharmaceutical compositions of the present invention may also include one or more of a colouring, sweetening or flavouring agent.

| EXAMPLES 1-2 | Weight/g | |
|---|---|---|
| | 1 | 2 |
| Carbomer 934P | 0.25 | 0.75 |
| Sodium hydroxide | 0.15 | 0.40 |
| Sodium bicarbonate | — | 0.75 |
| Methyl parabens | 0.36 | 0.36 |
| Propyl parabens | 0.10 | 0.10 |
| Water | to 100 ml | to 100 ml |

The carbomer was dispersed, with agitation in about 75 ml of water and aqueous sodium hydroxide was added to give a final product pH of 7.5 to 8.0. The sodium bicarbonate and methyl and propyl parabens were dispersed in 20 ml of water and added to the carbomer gel. Additional water was added to make up to a final volume of 100 ml followed by thorough mixing to produce a homogenous mixture.

2. ENEMAS

Aqueous retention enemas can be produced with similar compositions to Examples (1) and (2)

3. CAPSULES

Effective dispersion of the carbomer can be enhanced by the incorporation of disintegrating agents such as starch and its derivatives such as sodium starch glycollate and cellulose derivatives such as sodium carboxymethylcellulose and also by inclusion of effervescent combinations such as sodium bicarbonate-citric acid. Capsules were prepared from the following mixture.

| EXAMPLES 3-5 | Weight/mg | | |
|---|---|---|---|
| | 3 | 4 | 5 |
| Sodium carbomer 934P | 200 | 200 | 200 |
| Lactose | 200 | 150 | — |
| Citric acid | — | — | 105 |
| Sodium bicarbonate | — | — | 95 |
| Sodium starch glycollate | — | 10 | 8 |
| Talc | — | — | 3 |

Carbomer sodium salt was prepared by dispersing 1 kg of carbomer in a solution of 400 g sodium hydroxide in 3.6 kg anhydrous methanol. The salt was collected by filtration, dried and comminuted.

The formulation ingredients were blended to produce a uniform mix and appropriate dose weights taken and filled into suitable size capsule shells.

Capsules soluble at pH7 and above were produced by coating the capsule of Examples 3 to 5 with a polymer which is resistant to acid conditions. A suitable polymer is a polymethacrylate polymer Eudragit S (Rohm Pharma). This is an anionic polymer synthesised from methacrylic acid and methacrylic acid methyl ester; it is soluble at pH7 and above.

A solution suitable for capsule coating was prepared by dissolving the polymer in a suitable organic solvent e.g. ethanol, isopropanol or acetone. The solvent may contain dissolved therein a plasticiser such as a polyethylene glycol, dibutyl phthalate, triacetin at a concentration of 10-25% of the polymer weight. The concentration of polymer in the solvent was generally between 3 and 6% w/v.

The capsules were coated by suspending the capsules in a warm airstream and using a suitable spray gun to apply the coating solution until an acid impermeable coat thickness was achieved.

4. SACHET

When the contents of a sachet are added to water before drinking, effective dispersion of the carbomer is achieved by an effervescent base, for example a citric acid/sodium bicarbonate mix. Flavour, sweetening and colouring agents may also be included.

| EXAMPLES 6-9 | Weight/mg | | | |
|---|---|---|---|---|
| | 6 | 7 | 8 | 9 |
| Carbomer 934P | 200 | 400 | 600 | 3000 |
| Dextrose | 3000 | 2500 | 3000 | 6000 |
| Sodium bicarbonate | 400 | 500 | 400 | 2000 |

-continued

| EXAMPLES 6-9 | Weight/mg | | | |
|---|---|---|---|---|
| | 6 | 7 | 8 | 9 |
| Citric acid | 100 | 150 | 100 | 500 |
| Sodium carbonate | 100 | 50 | 100 | 500 |

The ingredients were blended to produce a uniform mix which was filled into sachets.

On reconstitution these formulae give a solution of pH between 6 and 7.

The interaction of polyacrylates with colonic mucus glycoprotein and the ability of polyacrylates to inhibit mucolysis by faecal enzymes has been investigated in in vitro and in vivo animal models and in human volunteers.

MUCUS VISCOSITY

Mucus gel scraped from the surface of pig or human colons was collected in a cocktail of proteinase inhibitors [1.0 mM phenylmethylsulphonyl fluoride (P.M.S.F), 50 mM iodoacetamide, 100 mM aminohexanoic acid, 5 mM benzamidine HCl, 1.0 mgl$^{-1}$ soybean trypsin inhibitor and 10 mM Na$_2$E.D.T.A in 0.5 M tris/HCl pH 8.0] (Hutton et al, Biochem. Soc. Trans. 15 (6), 1074 1987) and solubilised by mild homogenisation for 1 minute at full speed in a Waring blender. Insoluble material and tissue debris were removed by centrifugation for 1 hour at $2.4 \times 10^4$ g and 4° C. Glycoprotein was isolated from the solubilised gel, free from contaminating non-covalently bound protein and nucleic acid, by subjecting the extract to two equilibrium density gradient centrifugation steps in 3.5 M CsCl (Creeth and Denborough, Biochem. J., 177, 879–891 (1970); Starkey et al, Biochem. J. 141, 633–639 (1974)).

The solution viscosity of mucus glycoproteins and/or carbomer 934P was measured using a Contraves low shear cup and bob viscometer. Preparations of glycoprotein or polyacrylate were equilibrated with M/15 M KH$_2$PO$_4$/Na$_2$HPO$_4$ pH 7.5 (containing 50 mM NaCl) for 24 hours at 4° C. before use.

Mucolytic activity was measured quantitatively by the increase in free peptide N-terminals formed by proteolytic cleavage of the mucus peptide core, as described in the methodology section referring to the in-vitro analysis of human faecal proteolytic activity.

Table 1 presents data illustrating the percentage synergistic increase in specific viscosity of pig colonic mucus glycoprotein-carbomer 934P mixtures above the calculated additive viscosities of the mucus glycoprotein and carbomer 934P measured separately at a carbomer 934P concentration of 2.0 mg ml$^{-1}$ at pH 7.5 and 25° C.

TABLE 1

| Mucus mg ml$^{-1}$ | % Increase in Viscosity |
|---|---|
| 0.5 | 23 |
| 1.0 | 55 |
| 2.0 | 122 |
| 3.0 | 170 |
| 4.0 | 460 |

Table 2 presents data illustrating the percentage synergistic increase in specific viscosity of pig and human colonic mucus glycoprotein-carbomer 934P mixtures above the calculated additive viscosities of the mucus glycoprotein and carbomer 934P measured separately at a fixed mucus glycoprotein concentration of 1.0 mg ml$^{-1}$ at pH 7.5 and 25° C.

TABLE 2

| Carbomer 934P mg ml$^{-1}$ | % Increase in Viscosity | |
|---|---|---|
| | Pig | Human |
| 0.5 | 25 | 39 |
| 1.0 | 41 | 46 |
| 2.0 | 55 | 59 |
| 3.0 | 73 | 93 |
| 4.0 | 75 | 164 |

From Tables 1 and 2 it can be seen that carbomer 934P and mucus glycoprotein synergistically interact over a range of concentrations with colonic mucus. Similar interactions were observed for both pig and human colonic mucus.

PROTEOLYTIC ACTIVITY

Rat Faecal Proteolytic Activity (In-Vivo)

In the test method twelve male Sprague-Dawley rats weighing between 270 g and 290 g were individually housed for the duration of the study. During period 1 the animals were dosed with 2 ml of saline (control treatment) by gavage at between 12:00 and 12:30 hours daily for 5 days. In period 2, which commenced after a 4 day washout period, the animals were dosed with 20 mg/kg carbomer (test treatment) dissolved in 2 ml saline as above. Throughout periods 1 and 2 faeces from individual animals were collected each day over 24 hours (08:00 to 08:00 hours) on moist collecting papers then pooled and weighed. The material was thoroughly dispersed in anaerobic Tris buffer (0.1M, pH 7.0) containing 50 mM mercaptoethanol to a final concentration of 10%. The general protease substrate azocasein was used to determine faecal protolytic activity. An aliquot of 0.5 ml of a 10 mg/ml solution of azocasein was added in triplicate to an equal volume of each faecal slurry. Duplicate controls containing only substrate were set up and incubated simultaneously; the faecal slurry was added to these controls at the end of the incubation period. The reaction was quenched after 1 hour at 37° C. by the addition of 0.1 ml of 50% trichloroacetic acid (TCA). Precipitated material was removed by centrifugation at 11400 g for 5 mins. Supernatant (0.75 ml) was added to an equal volume of 1.0M NaOH and the absorbance of the resultant solution determined in a spectrophotometer at 450 nm. Extent of azocasein hydrolysis was determined from the intensity of TCA soluble coloured material and converted to concentration by a standard curve prepared from authentic azocasein. Specific protease activity in faeces was expressed as mg azocasein hydrolysed/hour/g wet weight faeces. The significance of the difference between protease activities and faecal outputs during periods 1 (control) and 2 (test) was determined using a students t-test. A treatment effect was considered significant if the p value was less than 0.05.

Table 3 presents test data showing effect of treatment with oral carbomer on rat faecal protease activity. Values presented are for 12 animals on placebo (control-treatment) and after 48 hours of carbomer (test-treatment)

TABLE 3

| Control-treatment | Protease Activity* Test-treatment | % Inhibition | p Value |
|---|---|---|---|
| 2.1 ± 0.2 | 1.3 ± 0.2 | 38 | <0.001 |

*mg azocasein hydrolysed/hr/g wet weight

Results presented in Table 3 demonstrate that treatment with oral carbomer significantly ($p<0.001$) reduced faecal protease activity in rats. An overall decrease of 38% was attained. These data indicate that orally dosed carbomer enters the rat colon and is effective in reducing faecal protease activity.

Human Faecal Proteolytic Activity (In-Vitro)

Human faecal extracts (from asymptomatic volunteers) were obtained by suspending samples of stool in 4 volumes of M/15M $KH_2PO_4/Na_2HPO_4$ pH 7.5 containing 50 mM NaCl and centrifuging at 10,000 g for 15 minutes at 4° C. The supernatant was retained as the faecal extract.

Proteolytic activity was measured using a modification of the method of Lin et al, J.Biol.Chem. 244 (4), 789-793 (1969), i.e. a sensitive trinitrobenzene sulphonic acid assay for formation of new peptide N-terminals using succinyl albumin as substrate. Faecal extract containing one unit of protease activity (equivalent to 1 μg trypsin) was mixed with 0.5 ml buffer (M/15 phosphate pH 7.5) or inhibitor. Substrate (0.5 ml, 8 mgml$^{-1}$ succinyl albumin) was added to start the reaction and samples were incubated for 30 minutes at 37° C. Four per cent (w/v) sodium bicarbonate (0.5 ml) and 0.05% (w/v) trinitrobenzene sulphonic acid were added to trinitrophenylate the free amino groups formed and samples were incubated at 50° C. for 10 minutes to develop colour.

10% (w/v) Sodium dodecyl sulphate (0.5 ml) and 1M HCl (0.25 ml) were added to complete the reaction. Absorbance at 340 nm was measured. All samples were compared with heat inactivated faecal extract controls (100° C., 10 minutes).

A linear increase in N-terminals formed by proteolytic cleavage of peptide bonds was found over the first 30 minutes of digestion. Freezing and thawing was found to have no effect on the proteolytic activity in the extracts. Proteolytic activity in faecal extracts against succinyl albumin was inhibited by soybean trypsin inhibitor (1 μg) and P.M.S.F. (1 mM) but not by iodoacetamide (50 mM) or $Na_2$ E.D.T.A. (10 mM). In view of this, levels of faecal protease activity were subsequently quantified as equivalents of porcine pancreatic trypsin activity by weight.

Table 4 presents data illustrating the % inhibition of faecal proteolytic activity by a range of concentrations of carbomer 934P at pH 7.5 and 37° C.

TABLE 4

| Carbomer 934P mg ml$^{-1}$ | % Inhibition | p value |
|---|---|---|
| 2.0 | 99.4 | <0.001 |
| 1.0 | 100 | <0.001 |
| 0.5 | 99.0 | <0.001 |
| 0.28 | 25.8 | <0.05 |
| 0.12 | 7.5 | <0.01 |

From Table 4 it can be seen that carbomer 934P over the range of concentrations 2.0-0.12 mgml$^{-1}$ significantly inhibited colonic proteolytic activity.

Table 5 presents data illustrating the effect of carbomer 934P compared with a range of other polymers on faecal proteolytic activity at pH 7.5 and 37° C.

TABLE 5

| Acidic Polymer | mg ml$^{-1}$ | % Inhibition | p value |
|---|---|---|---|
| Carbomer 934P | 2.0 | 99.4 | <0.001 |
| Carbomer 940 | 1.0 | 19.4 | <0.05 |
| Sodium alginate | 2.0 | 0 | — |
| Carageenan S | 2.0 | 0 | — |
| Carageenan G | 2.0 | 0 | — |

From Table 5 it can be seen that carbomer 934P possesses superior inhibition of faecal proteolytic activity when compared to a range of other polymers.

Table 6 shows the percentage inhibition of mucolysis achieved at pH 7.5 and 37° C. by varying concentrations of carbomer 934P in the presence of one unit of faecal protease activity (equivalent to 1 μg trypsin), 15 minute incubation time.

TABLE 6

| Carbomer 934P:protease (w/w) | % Inhibition |
|---|---|
| 190:1 | 8 |
| 600:1 | 56 |
| 1200:1 | 70 |

From Table 6 it can be seen that carbomer 934P inhibits proteolytic mucolysis in a dose related manner.

Human Faecal Proteolytic Activity (In-Vivo)

Twelve healthy, non-patient, male volunteers (mean age 35.5±13.4 years) were entered into a randomised, single-blind placebo cross-over study to determine the effect of oral carbomer on faecal protease activity. The volunteers were free living throughout the trial. Treatment periods lasted for 10 days during which each volunteer was dosed with either carbomer (0.4 g t.i.d. of Sachet formulation example 7) or placebo (t.i.d.) in water. Faeces were collected daily during the treatment periods and assayed on days 1,2,4,6,8 and 10. A 20% faecal slurry was prepared in anaerobic 0.5M Tris buffer (pH 7.0) containing 50 mM mercaptoethanol. The slurry was then fractionated into a washed bacterial cell fraction (WCF), a washed particulate fraction (WPF) and a supernatant fraction (SFF) by multistep centrifugation according to the scheme:

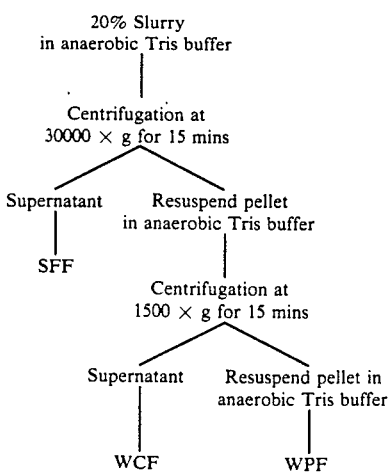

The fractions were diluted in an equal volume of anaerobic buffer and assayed for general protease activity using azocasein as substrate as described above. Concurrently each fraction from each sample was assayed for trypsin-like activity using benzoyl-arginine p-nitroamilide (BAPNA) by a mocification of the method of Appel, in: Methods in Enzymatic Analysis, 2nd Edn., Vol 2, pp 949–974, (1984). A 1.2 mM solution of BAPNA was prepared in anaerobic Tris buffer and added in triplicate to an equal volume (0.5 ml) of faecal material. Control assays were performed in duplicate by incubation of substrate only. These mixtures were incubated at 37° C. for 1 hour at which time the faecal fractions were added to control tubes and all reactions stopped by the addition of 0.1 ml of 50% TCA. Particulate and precipitated material was removed by centrifugation at 11400 g for 5 mins. Aliquots (0.75 ml) of the supernatant were added to 0.75 ml ice-cold sodium nitride solution (1.0 mg/ml) in fresh tubes. After 15 mins these tubes were warmed to room temperature and 0.75 ml of ammonium sulphamate (25 mg/ml) added. The assay tubes were incubated at room temperature for 20 mins to remove any nitrite still present. At this time 1.0 ml of 1.0 mg/ml N-1-Naphthyl-ethylenediamine dihydrochloride (chromogen) solution in methanol was added to develop colour. The absorbence of the solution at 546 nm was converted to nmol p-nitroaniline released using a standard p-nitroaniline absorbance curve and specific activities were expressed in terms of nmol p-nitroaniline released/hour/g wet weight of material (units). Statistical analysis was carried out using methodology described by Hills and Armitage, B. J. Clin. Pharmacol.8, 7–20, (1979).

Table 7 presents test data describing the effect of oral carbomer on human faecal trypsin-like activity as shown by BAPNA hydrolysis (Table 7a) and on general protease activity as shown by azocasein hydrolysis (Table 7b).

TABLE 7a

| | Trypsin-like activity (BAPNA hydrolysis) | | | |
|---|---|---|---|---|
| Fraction | Pre-treatment | Post-treatment | % Inhibition | p value |
| WCF | 20.1 | 12.1 | 40 | 0.01 |
| WPF | 27.4 | 15.5 | 43 | 0.03 | nmol p-nitroanilide released/hr/g wet weight

TABLE 7B

| | General protease activity (azocasein hydrolysis) | | | |
|---|---|---|---|---|
| Fraction | Pre-treatment | Post-treatment | % Inhibition | p value |
| WCF | 0.413 | 0.304 | 26 | =0.07 |
| WPF | 0.731 | 0.569 | 22 | =0.08 | mg azocasein hydrolysed/hr/g wet weight

Results obtained from the human volunteer study (Tables 7a and 7b) showed that on treatment with carbomer a highly significant reduction in trypsin-like activity (as shown by BAPNA hydrolysis) was attained in both the WCF (40% reduction; p=0.01) and the WPF (43% reduction; p=0.03) of faeces. General protease activity, as demonstrated with azocasein hydrolysis, was reduced in WCF by 26% (p=0.07) and in WPF by 22% (p=0.08). These data showed that carbomer when given orally as a solution in water entered the human large gut and produced a substantial reduction in protease activity.

The proteolytic activity in human faecal samples normally falls within the range of 30 to 300 $\mu g g^{-1}$, expressed as $\mu g$ trypsin equivalents per g wet weight of stool. It is envisaged that the inhibition of the proteolytic activity in human stools (average daily stool 150 g wet weight) will be achieved following the administration of polyacrylates, and particularly carbomer in the range 200 mg to 3 g per unit dose. The dose selected will be dependent on whether the treatment is for the maintenance of patients during the remission phase of active inflammatory bowel disease or whether used as a treatment therapy during the relapse phase of the disease when elevated levels of proteolytic activity are observed.

We claim:

1. A method for the treatment of conditions caused by mucolytic protease activity in the human intestinal tract, by reducing proteolytic activity therein which comprises administering to a patient an effective oral or rectal amount of a polyacrylate as the sole active ingredient.

2. A method according to claim 1 wherein the polyacrylate is carbomer or its sodium salt.

3. A method according to claim 2 wherein the polyacrylate is carbomer 934P. or its sodium salt.

4. A medicament for use in the method as claimed in claim 1 in unit dosage form containing from 200 mg to 3 g of the polyacrylate per unit dose.

5. A medicament as claimed in claim 4 wherein the polyacrylate is carbomer or its sodium salt.

6. A medicament as claimed in claim 5 wherein the polyacrylate is carbomer 934P or its sodium salt.

* * * * *